United States Patent
Kousaka et al.

(10) Patent No.: US 7,043,394 B2
(45) Date of Patent: May 9, 2006

(54) METHOD AND DEVICE FOR MEASURING FINE PARTICLES IN ULTRAPURE WATER

(75) Inventors: Yasuo Kousaka, Atsugi (JP); Mutsuko Endou, Atsugi (JP); Seiichi Inagaki, Atsugi (JP); Takazou Hirose, Atsugi (JP); Motonori Yanagi, Atsugi (JP)

(73) Assignee: Nomura Micro Science Co., Ltd., Atsugi (JP)

( * ) Notice: Subject to any disclaimer, the term of this patent is extended or adjusted under 35 U.S.C. 154(b) by 9 days.

(21) Appl. No.: 10/512,426

(22) PCT Filed: Apr. 25, 2003

(86) PCT No.: PCT/JP03/05298

§ 371 (c)(1),
(2), (4) Date: Oct. 25, 2004

(87) PCT Pub. No.: WO03/091707

PCT Pub. Date: Nov. 6, 2003

(65) Prior Publication Data

US 2005/0228610 A1 Oct. 13, 2005

(30) Foreign Application Priority Data

Apr. 25, 2002 (JP) .............................. 2002-124756

(51) Int. Cl.
*G01D 1/00* (2006.01)
*G06F 15/00* (2006.01)
*G06M 11/04* (2006.01)

(52) U.S. Cl. ...................... 702/128; 73/865.5

(58) Field of Classification Search ................ None
See application file for complete search history.

(56) References Cited

U.S. PATENT DOCUMENTS 4,817,446 A * 4/1989 Kanamori .................. 73/865.5

FOREIGN PATENT DOCUMENTS

| CA | 1276299 | 11/1990 |
|---|---|---|
| DE | 37 89 736 T2 | 1/1988 |
| EP | 0 254 380 A2 | 1/1988 |
| JP | 63-32347 A | 2/1988 |
| JP | 3-39635 A | 2/1991 |

OTHER PUBLICATIONS

Martin A, Cohen et al., "Observations Less than the Analytical Limit of Detection: A New Approach", The Journal of the Air & Waste Management Association (JAPCA Note-Book), Mar. 1989, pp. 328-329, vol. 39, No. 3.

"Testing methods for concentration of fine particles in highly purified water", Japanese Industrial Standard, JIS K 0554, 1995, (English) pp. 1-17, (Japanese) pp. 1-31.

* cited by examiner

*Primary Examiner*—John Barlow
*Assistant Examiner*—Sujoy Kundu
(74) *Attorney, Agent, or Firm*—Foley & Lardner LLP (57) ABSTRACT

A novel measuring method which allows measurement of fine particles which are extremely fine and contained in a very small amount in ultrapure water is provided. The number frequency with respect to the fine particles having a particle diameter of 0.1 μm or more is measured based on the finding that the fine particles contained in the ultrapure water at the use point of an ultrapure water production system exhibits a logarithmic normal distribution to determine the logarithmic normal distribution of the fine particles contained in the ultrapure water, and the number of the fine particles having a particle diameter of less than those of the measured particles contained in the ultrapure water is obtained from the distribution.

4 Claims, 8 Drawing Sheets

METHOD AND DEVICE FOR MEASURING FINE PARTICLES IN ULTRAPURE WATER

TECHNICAL FIELD

The present invention relates to a device and method for measuring fine particles in ultrapure water capable of measuring the number of fine particles having a particle diameter of less than 0.1 μm contained in the ultrapure water.

BACKGROUND ART

Ultrapure water is water very highly purified to have high purity which is obtained by a repeated operation of removing various types of impurities from water containing them. The ultrapure water having very high purity is now specially demanded in production of semiconductor devices which have become very large-scale devices highly miniaturized. A design rule for microfabrication of a semiconductor device has already reached 0.13 μm, and ultrapure water used for the production of semiconductor devices according to this design rule is demanded that the particle diameter of fine particles contained in it is one tenth of 0.13 μm or less. The number of fine particles having a particle diameter of 0.05 μm or more contained in ultrapure water is limited to, for example, 100/L or less.

In order to supply stably ultrapure water meeting the above-described provisions, it is required that a very small number of fine particles contained in the ultrapure water can be counted and monitored at all times.

Figure 9:
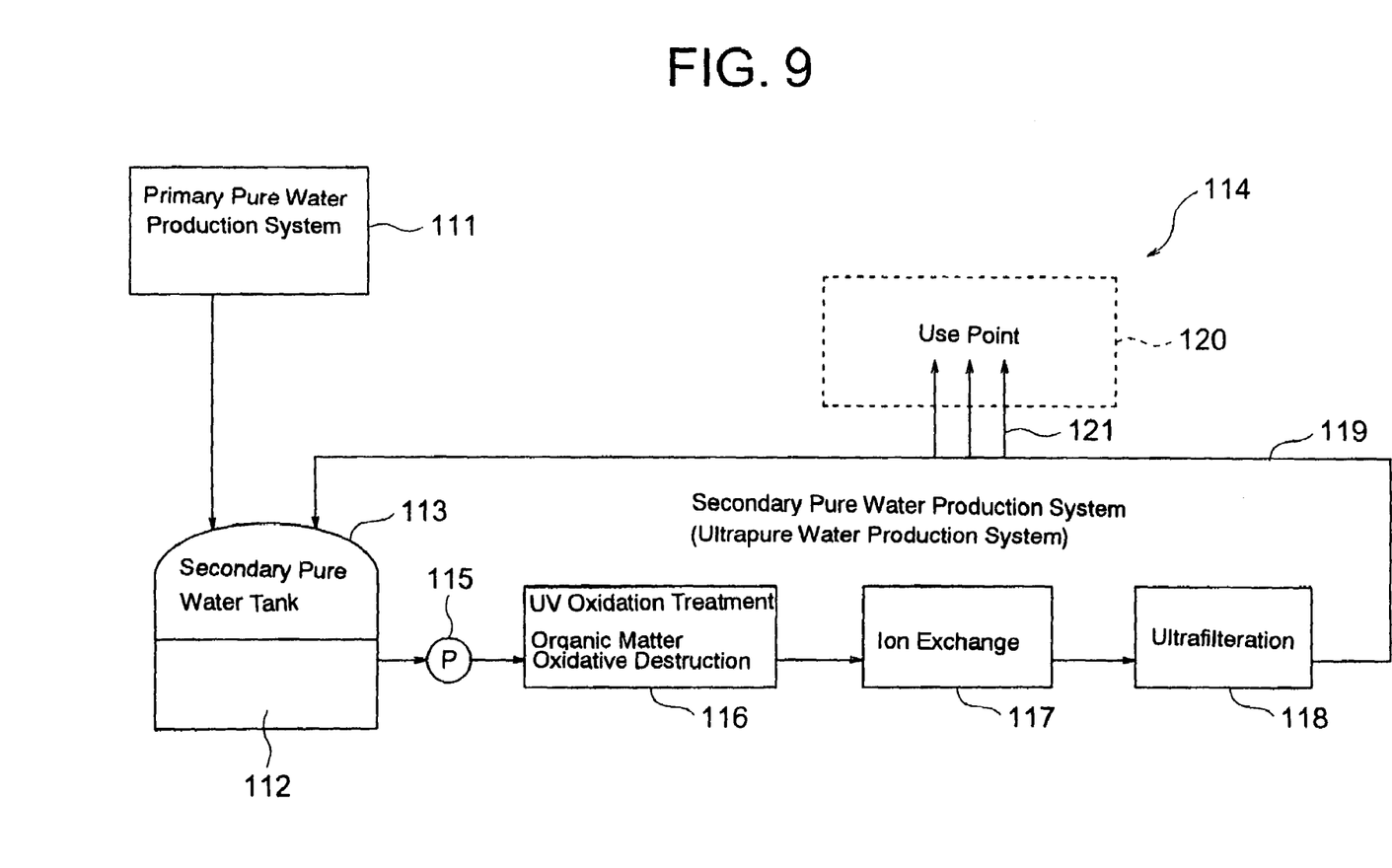
FIG. 9 is a diagram schematically showing an example of a plant for producing ultrapure water.

FIG. 9 is a diagram schematically showing an example of a conventional system for producing ultrapure water. In FIG. 9, a primary pure water treating system 111 produces pure water 112 by removing impurities from raw water such as city water by filtration, cation exchange, deaeration, anion exchange, and passing through an RO membrane. The produced pure water is stored in a secondary pure water tank 113.

A secondary pure water treating system 114 further purifies the pure water 112 to produce ultrapure water. The pure water 112 in the secondary pure water tank 113 is fed by a pump 115 to a UV oxidation treating device 116 where an organic matter is undergone oxidative destruction. The water is ion-exchanged by an ion-exchange tower 117, ultrafiltered by an ultrafilter 118, and supplied as ultrapure water 121 to a use point 120 for various types of usage through a pipe 119 without being stored. Remaining ultrapure water not used is not stored but returned to the secondary pure water tank 113.

For measurement and control of the purity of the ultrapure water produced as described above, it is necessary to measure fine particles contained as impurities in the ultrapure water. A conventional method for measuring fine particles having a particle diameter of 0.1 μm or more contained in the ultrapure water is specified and explained in detail in JIS K0554.

Such a conventional method for measuring fine particles in ultrapure water can be divided broadly into two types. One of them is a method by which a flow of ultrapure water is partly fed to a filtration film through the ultrapure water pipe 119 shown in FIG. 9, the ultrapure water is filtered by the filtration film to capture fine particles contained in it, and the captured fine particles are counted by observing through a microscope such as a scanning electron microscope. The other is a method using automatic fine particle measuring equipment for direct automatic measurement of fine particles in ultrapure water. For example, it feeds a flow of ultrapure water partly from the pure water pipe 119 shown in FIG. 9 to a flow cell, irradiates a laser beam to a flow of ultrapure water in the flow cell and measures the fine particles by using the laser beam scattered by the fine particles in the ultrapure water.

Among them, the method of capturing the fine particles in the ultrapure water by the filtration film and observing and counting the captured fine particles through the electron microscope has been used conventionally as a method capable of measuring the particles with high reliability because it can observe and count the particles closely and can count the particles directly. But, if the fine particles to be measured are very fine and have a particle diameter of, for example, less than 0.05 μm, it is necessary to raise a magnification of the microscope for observing, and time and efforts required for counting increase considerably because the number of fine particles is small.

For example, where ultrapure water containing 100 or less of fine particles having a particle diameter of 0.05 μm or more in one liter is filtered by a filtration film to capture and count the fine particles on the surface of the filter having a diameter of 25 mm and an effective diameter of about 20 mm, it is necessary to flow about one ton of ultrapure water. But, when the filtration film has a smaller pore diameter, a flow rate per unit area of the filter decreases sharply, and filtration time increases considerably. Therefore, if the filtration film has a pore diameter of 0.05 μm, the filtration velocity is slow, and the passage of one ton of ultrapure water takes several months. To monitor the fine particles contained in the ultrapure water and to preserve the quality of the ultrapure water, it is desired that the result is obtained soon, and even when more time is taken to count with high reliability, it is desired that the result is obtained in several days.

Where the fine particles captured by the filter have a smaller particle diameter, a magnification for measuring by observing through the electron microscope is set high, then a field of vision observable at a time becomes narrow, and the number of fields of vision for observing increases. Therefore, lots of time and efforts are required. Besides, the surface of the filter has initial-contaminated fine particles which are called blank particles, the fine particles to be measured have a size falling in a range of particle diameters of the blank particles, and the presence of the blank particles makes it more difficult to measure the fine particles having a small particle diameter in ultrapure water.

The method using the automatic fine particle measuring equipment, namely the method by which a flow of ultrapure water is guided to the flow cell, a laser beam is irradiated to the ultrapure water flowing in the flow cell, and the fine particles in the ultrapure water are measured by using the laser beam scattered by the fine particles in the ultrapure water, has a major advantage that the measured result can be obtained in a short time in comparison with the method of measuring the fine particles in ultrapure water by capturing them by a filter and observing through an electron microscope. Therefore, this method is useful as a measuring method, by which the fine particles in the ultrapure water are always measured and the measured result can be fed back to the control of the ultrapure water.

But, because the intensity of the scattered light from the fine particles is proportional to the 6th power of the particle diameter, the scattered light caused by the fine particles, which is a detection signal, becomes small sharply when the particle diameter becomes small. Meanwhile, output from a light receiver which receives the scattered light involves background noise such as noise from the device itself, scattering caused by the sample ultrapure water itself and the like. Because of the background noise, the minimum particle diameter of the fine particles in the ultrapure water, which can be taken out as a scattered light signal from the fine particles, is limited to about 0.05 µm, and the fine particles in the ultrapure water having a smaller particle diameter cannot be measured.

Japanese Patent Laid-Open Publication No. HEI 3-39635 discloses that scattered light is simultaneously detected by two detectors which are symmetrically disposed with respect to the optical axis, the detected signals are distinguished from background noise to allow measurement of a particle diameter of 0.07 µm or less. But, the ultrapure water has come to have a higher level of purity sharply in these years, so that the particle diameter of fine particles has become much smaller than a range of such particle diameters, and the number of fine particles has become smaller. Therefore, a novel measuring method over the conventional measuring methods is demanded as means for measuring fine particles in ultrapure water.

As described above, the measurement of fine particles which are fine and very few in ultrapure water by the conventional measuring means is quite difficult, and a novel measuring method capable of measuring such fine particles is demanded. The present invention has been made in view of the above circumstances and provides a novel measuring device and method enabling to measure inexpensively fine particles having a particle diameter of less than that of the measured fine particles in ultrapure water.

DISCLOSURE OF THE INVENTION

The present invention provides a device for measuring fine particles in ultrapure water, comprising a number frequency distribution measuring section for measuring a number frequency distribution of fine particles having a particle diameter of 0.1 µm or more in a number frequency distribution of fine particles contained in ultrapure water; and a logarithmic normal distribution calculating section for calculating a logarithmic normal distribution which has the number frequency distribution of fine particles having a particle diameter of 0.1 µm or more measured by the number frequency distribution measuring section as part of the distribution, wherein a number frequency distribution of fine particles having a particle diameter of less than the measured particle diameter of the fine particles contained in the ultrapure water is obtained from the logarithmic normal distribution calculated by the logarithmic normal distribution calculating section.

The particle diameter of the fine particles of which number frequency is measured is determined to be 0.1 µm or more according to the present invention, because the measurement can be made relatively easily and the grain size distribution can be derived with a relatively small margin of error when the particle diameter is 0.1 µm or more, but it suddenly becomes hard to measure when the particle diameter is less than 0.1 µm.

The present invention has been achieved as a result of advanced studies on the basis of a significant finding that a grain size distribution of fine particles in ultrapure water indicates a logarithmic normal distribution as a result of repeated measurement of a particle diameter of fine particles at a use point of a real plant in a steady operation for production of ultrapure water by observing through an electron microscope.

BEST MODE FOR IMPLEMENTING THE INVENTION

Figure 1:
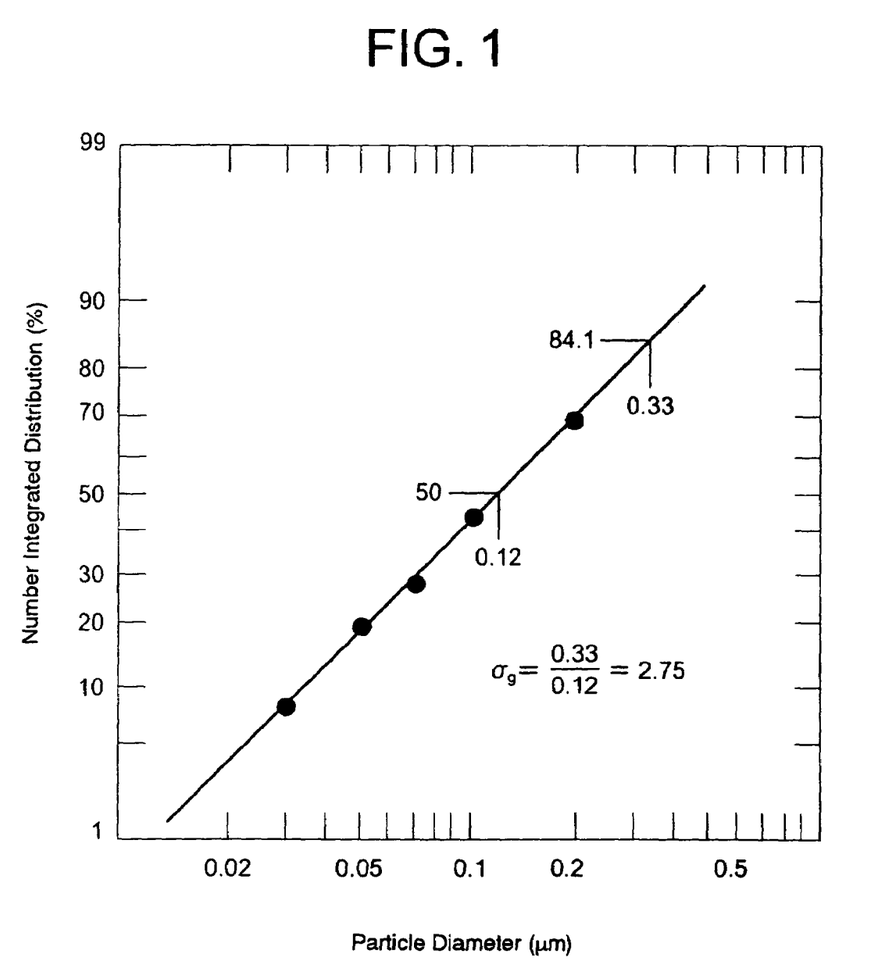
FIG. 1 is a diagram determined by measuring a number integrated distribution of fine particles in ultrapure water, which are collected by filtering from a real plant in steady operation for production of ultrapure water, by observing through an electron microscope, and plotting on logarithmico-normal probability paper.

FIG. 1 is an example of a number integrated distribution of fine particles obtained by taking a picture of fine particles in ultrapure water, which are collected by filtering from a real plant in steady operation for producing ultrapure water, by a scanning electron microscope, analyzing the image and measuring a particle diameter. The measurement was made according to JIS K-0554 (1995) "Testing Methods for Concentration of Fine Particles in Highly Purified Water", a filtration film having a pore diameter of 0.03 µm different from the JIS was used, and fine particles having a particle diameter of 0.03 µm or more were measured. The filtration film having a pore diameter of 0.03 µm had a filtration velocity of about one to several mL/minute. It took about three months to trap particles by filtering, the surface of the filtration film after filtering was observed through a scanning electron microscope, and a particle diameter (the longest diameter on a screen) and the number of particles were measured. FIG. 1 is a diagram obtained by calculating a number integrated distribution from the measured result and plotting on logarithmico-normal probability paper. FIG. 1 shows that the number of fine particles was integrated in increasing order of a particle diameter.

As exemplified in FIG. 1, the number integrated distribution of fine particles contained in ultrapure water at a use point of an ultrapure water producing plant lies on a substantially straight line when plotted on logarithmico-normal probability paper. Therefore, a grain size distribution of fine particles indicates a logarithmic normal distribution.

Because the fine particles contained in ultrapure water at a use point show the logarithmic normal distribution, the entire grain size distribution of the fine particles contained in the ultrapure water can be determined from the result of measuring a part of the grain size distribution instead of measuring the entire grain size distribution.

When the fine particles in the ultrapure water have a logarithmic normal distribution, the number of fine particles having a particle diameter of less than the measured particle diameter can be derived more accurately by accurately measuring particles having a particle diameter of 0.1 μm or more instead of using a measured value having a large margin of error by conducting difficult measurement of a smaller particle diameter side of the grain size distribution.

The fine particles showing the logarithmic normal distribution are often found in particles produced by a phase change from a liquid phase or a gas phase and also in those which are in a naturally occurred state without addition of an artificial operation in many fields such as aerosol science, colloid science and the like. It is considered that the fine particles in ultrapure water generate because of a naturally occurring probability event in the same manner as the former particles.

A number frequency distribution measuring section of the device for measuring the fine particles in ultrapure water according to the present invention can be provided with a fine particles capturing section for capturing the fine particles contained in the ultrapure water by a filtration film and a measuring section for measuring the fine particles contained in the ultrapure water captured by the filtration film by observing through a microscope.

The filtration film used here is a membrane filter of which pore diameter is controlled, and preferably a material for the filtration film (membrane filter) which has the pore diameter precisely controlled to the order of submicron by etching after irradiation of high-energy particles to the material.

As the microscope apparatus, a transmission optical microscope or an electron microscope which can provide magnifying power sufficient to observe submicron particles can be used. Especially, a scanning electron microscope which can observe directly the surface of a filtration film can be used favorably. As the above-described microscope apparatus, another scanning type microscope, such as a scanning atomic force microscope or a scanning tunneling microscope can also be used.

According to the present invention, it is adequate by capturing fine particles having a particle diameter of 0.1 μm or more among those contained in ultrapure water, so that the membrane filter can be determined to have a larger pore diameter so to increase a flow rate of pure water passing through the membrane filter. Thus, a filtering time duration for capturing the fine particles contained in the ultrapure water can be prevented from becoming long. And, where the number frequency distribution of fine particles is measured, limitation to fine particles having a particle diameter of 0.1 μm or more can prevent time and labor required to observe and measure the fine particles through a microscope from becoming excessive.

In the device for measuring fine particles in ultrapure water according to the present invention, the number frequency distribution measuring section can be provided with a flow cell section for taking in and flowing the ultrapure water to be supplied to a use point, an irradiation section for irradiating a laser beam to the ultrapure water flowing through the flow cell section, and a scattered light detecting and counting section for detecting scattered light of the laser beam which is scattered by the fine particles in the ultrapure water and counting the fine particles.

According to the present invention, only the fine particles having a particle diameter of 0.1 μm or more may be measured among those contained in ultrapure water, so that the fine particles having a particle diameter of less than the measured particle diameter can be determined in a relatively short time duration by measuring fine particles having a particle diameter which can be measured by a particle counting device using laser beam scattering. Therefore, fine particles having a particle diameter in a range of about 0.03 μm to about 0.5 μm are continuously measured by this device while an ultrapure water plant is operating, and the measured result can be used for control of the plant.

In the device for measuring fine particles in ultrapure water, the particle counting device using scattering of a laser beam can be provided with plural signal identifying sections having a different threshold value. Thus, plural number integrated values of fine particles having a particle diameter larger than that corresponding to the threshold value can be measured. A logarithmic normal distribution of the fine particles in ultrapure water can be calculated by preparing the required number of the number integrated values.

The method for measuring fine particles in ultrapure water according to the present invention comprises a number frequency distribution measuring step for measuring a number frequency distribution of fine particles having a particle diameter of 0.1 μm or more in a number frequency distribution of fine particles contained in ultrapure water; and a logarithmic normal distribution calculating step for calculating a logarithmic normal distribution which has the number frequency distribution of fine particles having a particle diameter of 0.1 μm or more measured by the number frequency distribution measuring step as part of the distribution, wherein a number frequency distribution of fine particles having a particle diameter of less than the measured particle diameter of the fine particles contained in the ultrapure water is obtained from the logarithmic normal distribution calculated by the logarithmic normal distribution calculating step.

EMBODIMENT 1

For particles showing a decided logarithmic normal distribution of a grain size distribution according to number frequency distribution data on the side of a larger particle diameter, when the integrated number of particles having a particle diameter up to D is determined to be n, a logarithmic number frequency distribution dn/d (log D) indicating a rate of change of n to log D is represented by the following expression 1.

$$\frac{dn}{d(\log D)} = \frac{N}{2\pi \log \sigma_g} \exp\left[-\frac{(\log D - \log D_g)^2}{2(\log \sigma_g)^2}\right] \quad \text{[Expression 1]}$$

where, N is the total number of particles; and $D_g$ determined by the following expression 2 is a geometric mean particle diameter of a particle diameter D and also an amount called as a geometric average particle diameter.

$$\log D_g = \frac{\sum n \log D}{N} \quad \text{[Expression 2]}$$

Besides, $\log \sigma_g$ is a logarithmic standard deviation determined by the following expression 3.

$$\log \sigma_g = \sqrt{\frac{\sum n(\log D - \log D_g)^2}{N}} \quad \text{[Expression 3]}$$

Figure 2A:
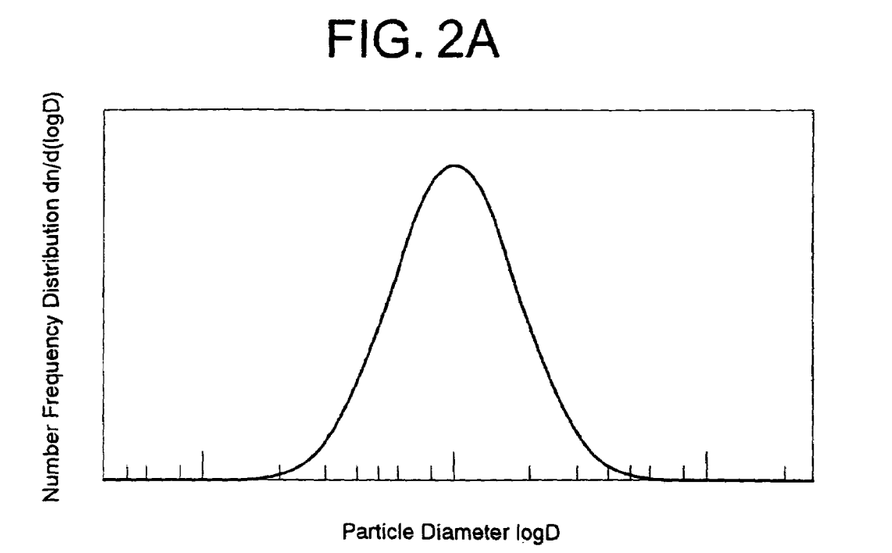
FIG. 2A and FIG. 2B are diagrams showing a number frequency distribution and a number integrated value of fine particles schematically showing a logarithmic normal distribution with the horizontal axis indicating a logarithmic scale.

The number frequency distribution represented by the expression 1 is schematically shown as seen in FIG. 2A with the particle diameter indicated on the horizontal axis having a logarithmic scale. And, a particle number integrated value n is schematically shown as seen in FIG. 2B with the particle diameter indicated on the horizontal axis having a logarithmic scale.

According to the present invention, a grain size distribution is measured for the large particle diameter of fine particles having a particle diameter of 0.1 µm or more in ultrapure water indicating a logarithmic normal distribution. Based on the fact that the measured data conforms with an expression of logarithmic normal distribution determined by the expression 1, parameters N, $D_g$ and $\sigma_g$ in the expression 4 are determined, and a distribution of fine particles in ultrapure water is determined. The parameters may be determined from the measured data such that, for example, a deviation squares sum of a measured value and a value given by the logarithmic normal distribution is minimized.

According to the present invention, a logarithmic normal distribution of fine particles can be determined easily from the measured data by using the following procedure.

Figure 2B:
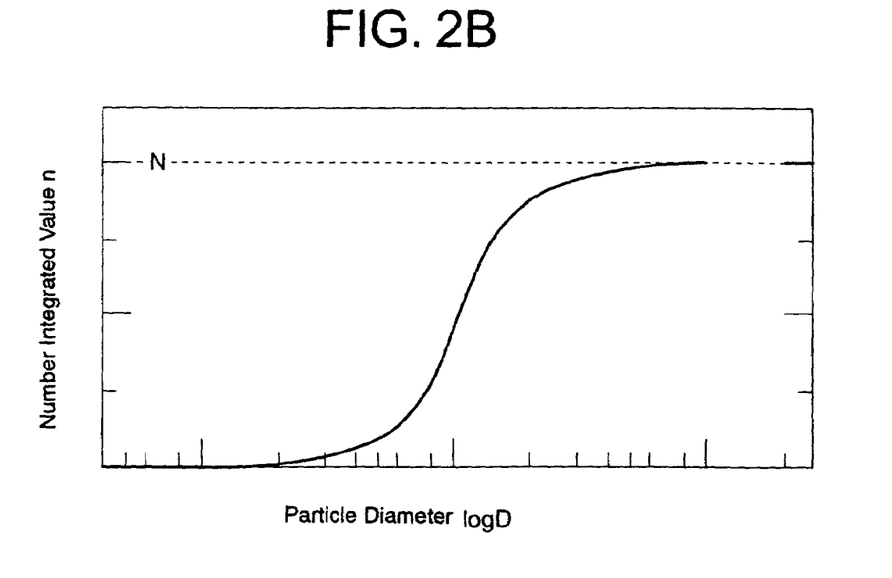

For the curve of the number integrated value n of the fine particles showing the logarithmic normal distribution as seen in FIG. 2B, n is divided by N to standardize so to determine the number integrated distribution of fine particles as n/N, and the vertical axis of N/n can be plotted with inverse function f−1(x) of a function (as shown in the expression 4) indicating an integrated distribution in a normal distribution as the scales to represent by a straight line as indicated by the solid line A of FIG. 1.

$$y = f(x) = \frac{1}{\sqrt{2\pi}} \int_{-\infty}^{x} \exp\left(-\frac{t^2}{2}\right) dt \quad \text{[Expression 4]}$$

Thus, logarithmico-normal probability paper has the horizontal axis indicating a logarithmic scale and the vertical axis indicating the f−1(x) as graduations, and an integrated distribution of fine particles having a logarithmic normal distribution is indicated as a straight line on the logarithmico-normal probability paper.

Therefore, the grain size distribution of fine particles having the logarithmic normal distribution can be determined as follows. First, the integrated value n is determined from the measured data about number frequency distribution dn/d (logD) of fine particles. Then, the total number N of the fine particles is determined so that the integrated distribution n/N forms a straight line on the logarithmico-normal probability paper. As the straight line of n/N obtained by the determined N, the grain size distribution of fine particles having the logarithmic normal distribution can be determined.

Even if the total number N of fine particles cannot be counted directly according to this method, three or more plural number integrated values from the larger particle diameter side are determined, the total number N of fine particles is assumed, a value obtained by dividing the number integrated value by N is plotted on the logarithmico-normal probability paper, and the value N can be determined so that the points plotted become closest to the straight line on the logarithmico-normal probability paper.

The straight line obtained here is a straight line on the logarithmico-normal probability paper indicating the logarithmic normal distribution of the fine particles. On the straight line indicating the logarithmic normal distribution, a geometric mean particle diameter (or geometric average particle diameter) $D_g$=0.12 µm of the particle diameter D is obtained as the particle diameter that the counted number distribution becomes 50%, and a geometric standard deviation $\sigma_g$=2.75 is obtained from the inclination of the straight line (a ratio between a logarithm of a particle diameter of an integrated distribution of 84.1% and a logarithm of a particle diameter of an integrated distribution of 50%).

Figure 3:
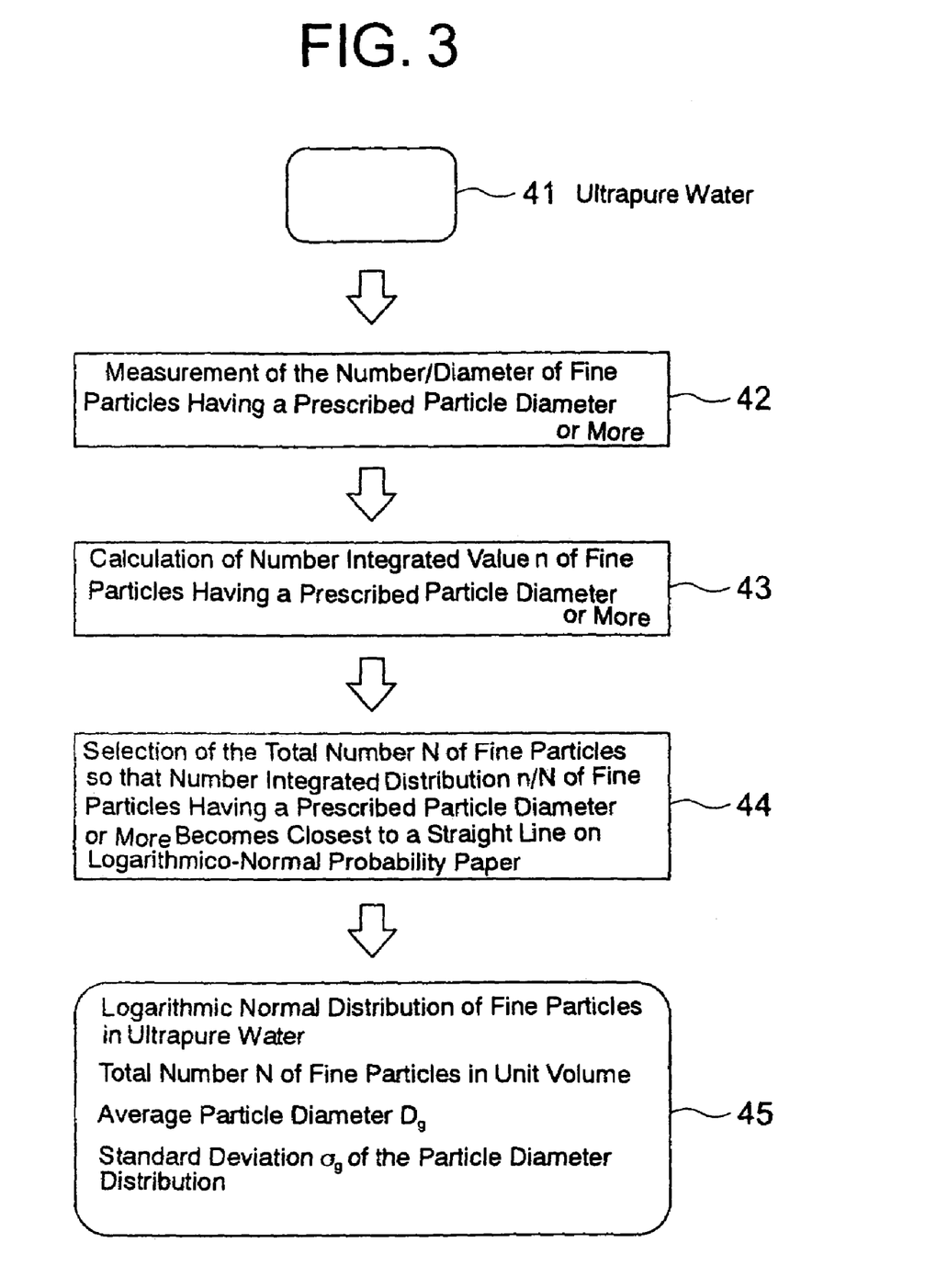
FIG. 3 is a flow chart showing a procedure of determining a logarithmic normal distribution of fine particles in ultrapure water in an embodiment of the present invention.

FIG. 3 shows the above-described procedure as a simplified flow chart. Ultrapure water 41 from a use point produced by the device for producing ultrapure water is subjected to measurement 42 of the number and particle diameter of fine particles having a prescribed particle diameter or more, and calculation 43 of number integrated value n(D) of the fine particles having a prescribed particle diameter or more is conducted. The number integrated value n of the fine particles having the prescribed particle diameter or more may be obtained directly without measuring the particle diameters of the individual fine particles. Subsequently, with respect to the number integrated value n(D) of the fine particles having D=0.1 µm or more, determination of the total number N of fine particles in ultrapure water having a prescribed volume so that n(D)/N becomes a straight line, or decision 44 of N and the straight line on the logarithmico-normal probability paper such that a sum of squares of a deviation between the straight line and the plot of n(D)/N on the logarithmico-normal probability paper becomes minimum is made. Thus, the total number N of fine particles in the ultrapure water having the prescribed volume is determined, and decision 45 on the logarithmic normal distribution of the fine particles in the ultrapure water, the mean particle diameter $D_g$ as its parameter, and the standard deviation $\sigma_g$ of the particle diameter distribution is obtained from the obtained straight line.

In FIG. 3, 41 denotes the ultrapure water, 42 denotes the measurement of a particle diameter of fine particles having a prescribed particle diameter or more, 43 denotes the calculation of the number integrated value of fine particles, 44 denotes the determination of the total number N of fine particles, and 45 denotes the logarithmic normal distribution of fine particles in ultrapure water.

EMBODIMENT 2

Measurement by Capturing Fine Particles by Filtration Film and Observing Through Electron Microscope The method of measuring by capturing fine particles in ultrapure water by a filtration film and observing through an electron microscope is conducted according to the description in JIS K-0554 (1995) "Testing Methods for Concentration of Fine Particles in Highly Purified Water". A filtration film having a pore diameter of 0.1 µm (Nuclepore membrane filter) is used for capturing and the captured fine particles having a particle diameter of 0.1 µm or more are measured by observing through an electron microscope to determine a number frequency distribution and a number integrated value.

Figure 4:
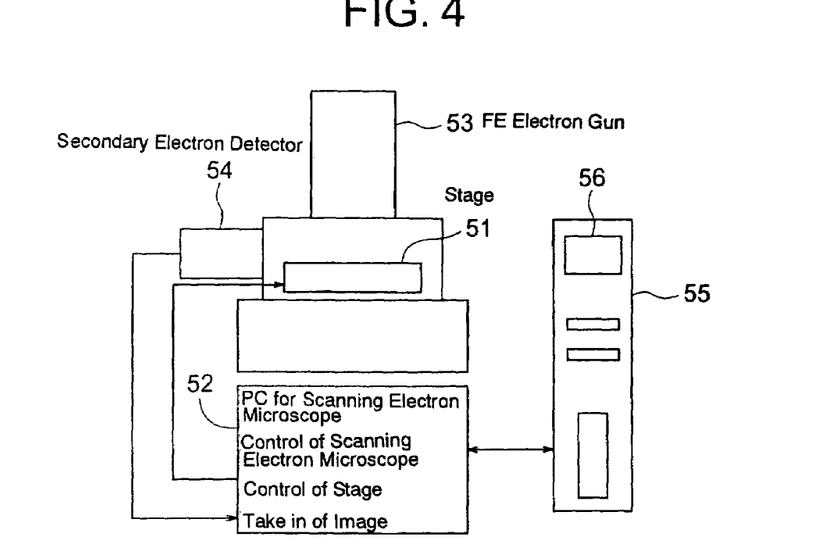
FIG. 4 is a diagram schematically showing the structure of a measuring device based on a scanning electron microscope.

FIG. 4 is a diagram schematically showing the structure of a measuring device based on a scanning electron microscope. The membrane filter having captured fine particles in ultrapure water is set on a stage 51 of the scanning electron microscope and scanned by an electron beam from an FE electron gun 53 under control by a signal from a computer 52 for the scanning electron microscope. The stage 51 of the scanning electron microscope where the sample is set is motor-driven according to a stage control signal from the computer 52 for the scanning electron microscope. Secondary electrons from the sample are caught by a secondary electron detector 54, and the signal is taken as image data into the computer 52 for the scanning electron microscope. The taken image signal data is sent to an image processing computer 55 and undergone image processing. The result is shown on a display section 56.

Figure 5:
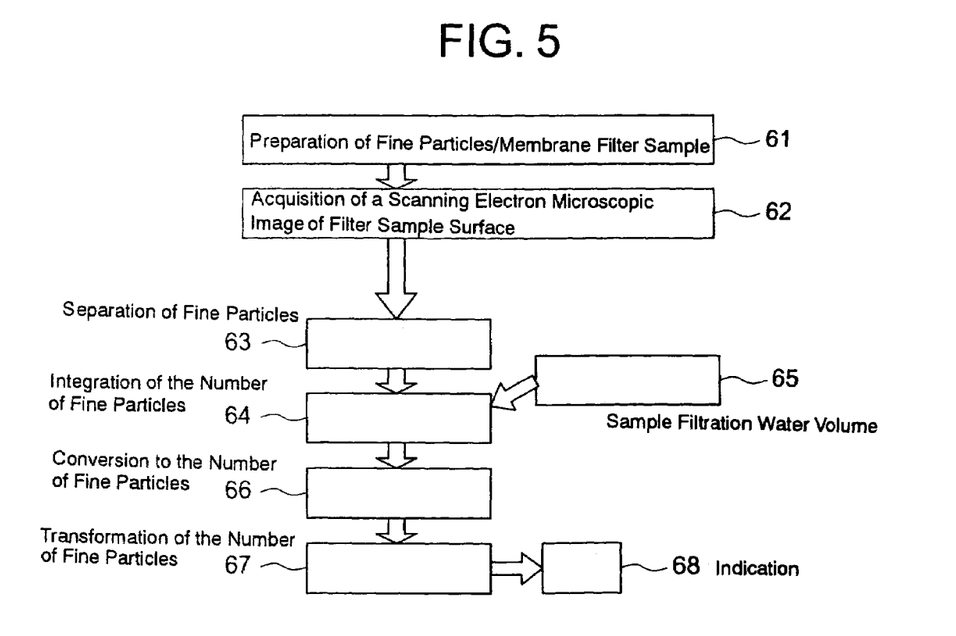
FIG. 5 is a diagram showing a flow of processing to measure fine particles by a scanning electron microscope.

FIG. 5 shows a flow of processing to measure fine particles by image processing of the surface of a membrane filter sample by the scanning electron microscope. The surface of the filter having captured the fine particles and subjected to sample preparation 61 is scanned by an electron beam for acquisition 62 of a scanning electron microscopic image, separation 63 of the fine particles is conducted by the internal processing by the image processing computer, integration 64 of the number of fine particles is conducted, conversion 66 to the number of fine particles per unit volume is conducted by inputting a volume of filtered water used for sampling of the fine particles, and conversion 67 of the number of fine particles is conducted to derive the fine particles having a small particle diameter. Display 68 of the results is conducted.

The fine particles observed here are generally not spherical, so that the diameters measured have a different value depending on a direction of measuring the fine particles. Therefore, measuring rules can be determined to adopt, for example, a rule of measuring the maximum diameter of each particle. Besides, there can be adopted a rule of determining an average value of the maximum and minimum diameters or a rule of determining a prescribed direction and measuring a diameter from the prescribed direction. Any of the above conditions may be selected in conformity with a purpose to conduct the measurement.

Referring to the logarithmic normal distribution of ultrapure water shown in FIG. 1, about 58% of all fine particles forming the grain size distribution is measured by measuring fine particles having a particle diameter of 0.1 μm or more for the grain size distribution of FIG. 1.

When the pore diameter of the Nuclepore filter is changed from 0.1 μm to its ½, namely 0.05 μm, the flow rate of the filter per unit area decreases to about one sixth of that when the pore diameter is 0.1 μm, resulting in taking a long time duration for filtering. Therefore, it is known that a method of deciding a grain size distribution by using the Nuclepore filter having a pore diameter of 0.1 μm and measuring a larger particle diameter side of the grain size distribution is very advantageous.

EMBODIMENT 3

Measurement of Fine Particles by Using Scattering of Laser Beam

Figure 6A:
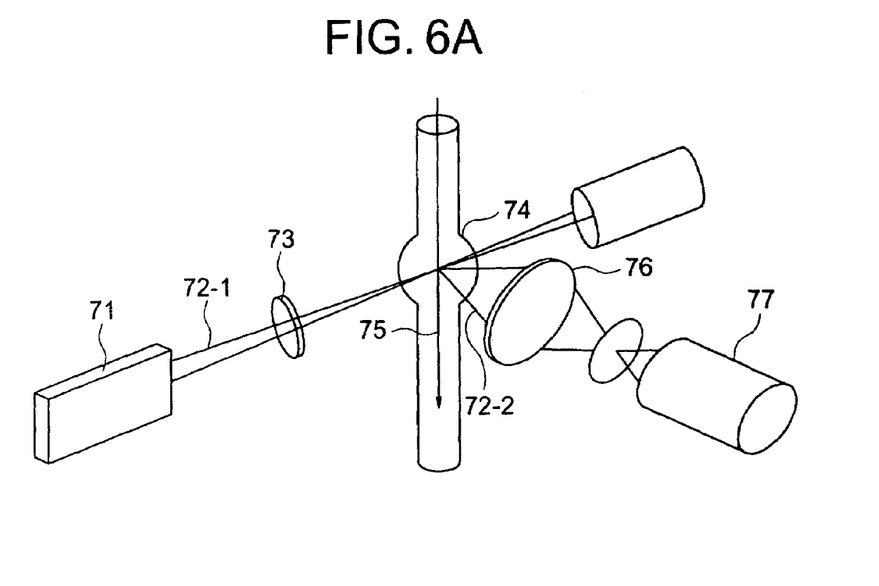
FIG. 6A and FIG. 6B are diagrams schematically showing an automatic device for measuring fine particles in ultrapure water.
Figure 6B:
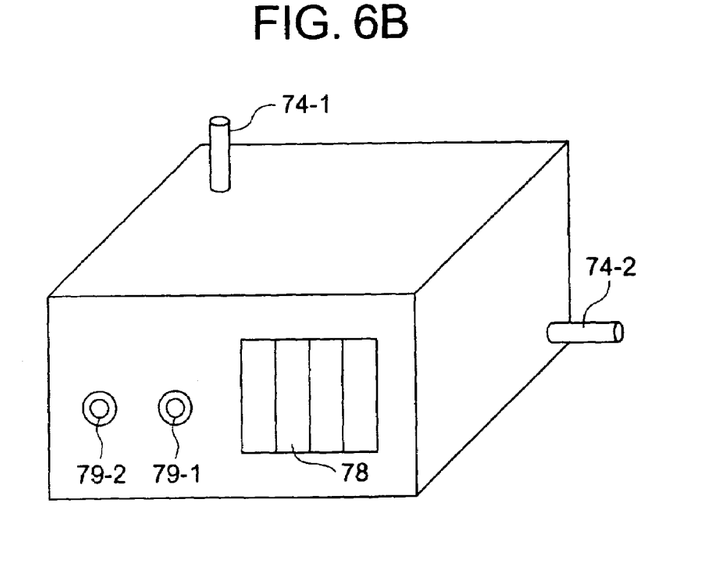

Fine particles in ultrapure water can be measured by using automatic measuring equipment for fine particles in ultrapure water schematically shown in FIG. 6A and FIG. 6B. In FIG. 6A, a light beam 72-1 emitted from a laser device 71 of a measuring section is irradiated to ultrapure water 75, which flows through a circular fine particle detecting region in a flow cell 74, by a projector lens 73. Scattered light 72-2 which is scattered by fine particles in the ultrapure water enters a light receiver 77 via a light-receiving lens system 76, and a light reception signal is detected.

FIG. 6B is a perspective diagram schematically showing the exterior of fine particles in the ultrapure water. In FIG. 6B, the ultrapure water enters through an inlet 74-1 of the flow cell and flows out through an outlet 74-2 of the flow cell. The measured result is shown on a display section 78, and the indication can be changed by a display changeover switch 79-1. A switch 79-2 is a power switch.

Figure 7:
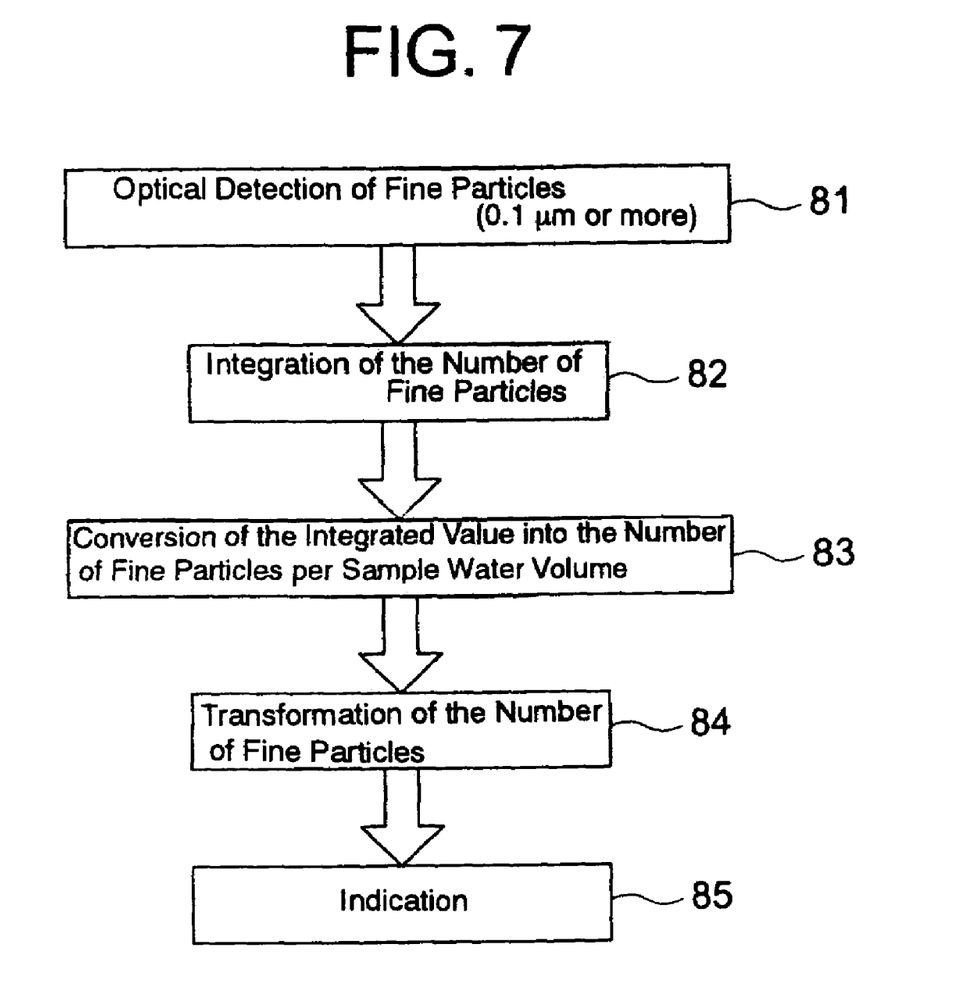
FIG. 7 is a diagram showing a flow of processing to measure fine particles by the automatic device for measuring fine particles.

FIG. 7 is a diagram showing a flow of processing to measure fine particles by the automatic fine particle measuring equipment. In FIG. 7, optical detection 81 of fine particles having a particle diameter of 0.1 μm or more is conducted, integration 82 of the number of fine particles is conducted, and conversion 83 of the integrated value into the number of fine particles per unit sample water volume is conducted. The result is used to conduct transformation 84 of the number of fine particles in order to determine the number of fine particles having a small particle diameter of 0.1 μm or less. And, indication 85 of the result is executed. In FIG. 7, 81 indicates the optical detection of fine particles, 82 indicates the integration of the number of fine particles, 83 indicates the conversion of the number of fine particles, 84 indicates the transformation of the number of fine particles, and 85 indicates the indication of the result.

EMBODIMENT 4

Comparison Between Derivation from Measurement of Particles Having a Particle Diameter of 0.1 μm or More and Direct Measurement For fine particles in ultrapure water at a use point of an ultrapure water producing plant, particles having a particle diameter of 1 μm or more were measured, and the result of deriving the fine particles having a particle diameter of 0.05 μm or more according to the logarithmic normal distribution was compared with the result obtained by directly measuring the particles having a particle diameter of 0.05 μm or more in the ultrapure water. The measuring means was a method by which a membrane filter was used to capture the fine particles in the ultrapure water by filtering for a long time duration, and a scanning electron microscope was used. The sample ultrapure water to be measured is ultrapure water in a really operating ultrapure water plant.

Figure 8:
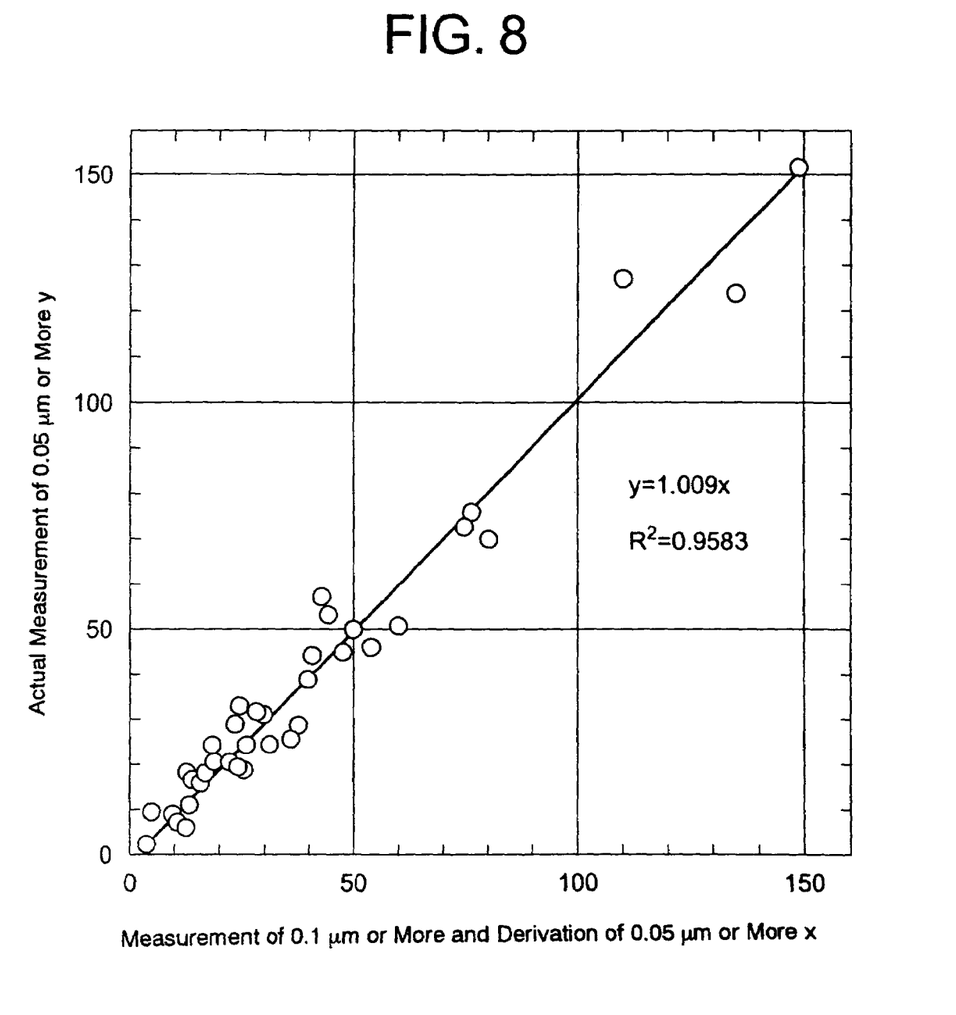
FIG. 8 is a diagram showing a relationship between the number of fine particles in ultrapure water derived by measuring the particles having a particle diameter of 0.1 µm or more and that derived by direct measuring.

The results are shown in FIG. 8. In FIG. 8, the number of fine particles x having a particle diameter of 0.05 μm or more is indirectly derived by using a logarithmic normal distribution by measuring fine particles having a particle diameter of 0.1 μm or more in ultrapure water is indicated along the horizontal axis, and the number of fine particles y having a particle diameter of 0.05 μm or more in ultrapure water directly measured is indicated along the vertical axis to examine the relationship between x and y. As a result, y=1.009x was obtained as a regression line, and dispersion R2=0.9583 and an agreement of x and y were obtained. In FIG. 9, 111 indicates a primary pure water treating system, 112 indicates pure water, 113 indicates a secondary pure water tank, 114 indicates a secondary pure water treating system, 115 indicates a pump, 116 indicates a UV oxidation treating device, 117 indicates an ion exchange tower, 118 indicates an ultra filter, 119 indicates a pipe, 120 indicates a use point, and 121 indicates ultrapure water.

It was confirmed from the above results that a particle diameter can be measured adequately and correctly by measuring fine particles according to the present invention.

The present invention relates to a device and method for measuring fine particles in ultrapure water, and the principle of the present invention can be applied extensively in addition to the measurement of fine particles in ultrapure water. For example, when a device for measuring fine particles in a high-purity solution (liquid medicine), a high-purity gas or a clean processing device is verified to be in conformity with the principle shown in the embodiment 1, the present invention can also be applied to measuring equipment provided with functions similar to the number frequency distribution measuring section and the logarithmic normal distribution calculating section according to the present principle.

INDUSTRIAL APPLICABILITY

According to the present invention, it has become possible to obtain a grain size distribution of fine particles by measuring a large particle diameter which is easily measured among fine particles in ultrapure water, and it has become possible to conduct conventionally difficult measurement of the grain size distribution of fine particles in ultrapure water easily and inexpensively.

What is claimed is:

1. A device for measuring fine particles in ultrapure water, comprising:
    a number frequency distribution measuring section for measuring a number frequency distribution of fine particles having a particle diameter of 0.1 µm or more in a number frequency distribution of fine particles contained in ultrapure water; and
    a logarithmic normal distribution calculating section for calculating a logarithmic normal distribution which has the number frequency distribution of fine particles having a particle diameter of 0.1 µm or more measured by the number frequency distribution measuring section as part of the distribution,
    wherein, a number frequency distribution of fine particles having a particle diameter of less than the measured particle diameter of the fine particles contained in the ultrapure water is obtained from the logarithmic normal distribution calculated by the logarithmic normal distribution calculating section.

2. The device for measuring fine particles in ultrapure water according to claim 1,
    wherein the number frequency distribution measuring section comprises a fine particle capturing section for capturing the fine particles contained in the ultrapure water by a filtration film and a measuring section for measuring the fine particles contained in the ultrapure water captured by the filtration film by observing through a microscope.

3. The device for measuring fine particles in ultrapure water according to claim 1,
    wherein the number frequency distribution measuring section comprises:
        a flow cell section for taking in and flowing the ultrapure water to be supplied to a use point;
        an irradiation section for irradiating a laser beam to the ultrapure water flowing through the flow cell section; and
        a scattered light detecting and counting section for detecting and counting scattered light of the leaser beam scattered by the fine particles in the ultrapure water.

4. A method for measuring fine particles in ultrapure water, comprising:
    a number frequency distribution measuring step for measuring a number frequency distribution of fine particles having a particle diameter of 0.1 µm or more in a number frequency distribution of fine particles contained in ultrapure water; and
    a logarithmic normal distribution calculating step for calculating a logarithmic normal distribution which has the number frequency distribution of fine particles having a particle diameter of 0.1 µm or more measured by the number frequency distribution measuring section as part of the distribution,
    wherein a number frequency distribution of fine particles having a particle diameter of less than the measured particle diameter of the fine particles contained in the ultrapure water is obtained from the logarithmic normal distribution calculated by the logarithmic normal distribution calculating section.

* * * * *